| United States Patent [19] | [11] Patent Number: 5,021,418 |
| Quagliato et al. | [45] Date of Patent: Jun. 4, 1991 |

[54] ANTIHYPERTENSIVE BENZOPYRAN COMPOUNDS

[75] Inventors: Dominick A. Quagliato, Edison; David D. Deininger, New Brunswick, both of N.J.

[73] Assignee: American Home Products Corporation, New York, N.Y.

[21] Appl. No.: 580,902

[22] Filed: Sep. 11, 1990

Related U.S. Application Data

[62] Division of Ser. No. 417,350, Oct. 5, 1989, Pat. No. 4,983,612.

[51] Int. Cl.$^5$ .................... A61K 31/495; C07D 487/04
[52] U.S. Cl. .................................. 514/249; 514/258; 544/280; 544/350

[58] Field of Search ................ 544/280, 350; 514/249, 514/258

[56] References Cited

U.S. PATENT DOCUMENTS 4,889,852 12/1989 Hartog et al. ...................... 514/249

FOREIGN PATENT DOCUMENTS 158923 12/1985 European Pat. Off. .

Primary Examiner—Mukund J. Shah
Assistant Examiner—Jyothsna Venkat
Attorney, Agent, or Firm—Walter Patton

[57] ABSTRACT

Disclosed herein are novel benzopyrans having pharmacological activity, to a process for preparing them, to pharmaceutical compositions containing them, and to their use in the treatment of hypertension.

5 Claims, No Drawings

ANTIHYPERTENSIVE BENZOPYRAN COMPOUNDS

This is a divisional application of copending application U.S. Ser. No. 07/417,350, filed Oct. 5, 1989 now U.S. Pat. No. 4,983,612.

BACKGROUND OF THE INVENTION

The present invention relates to novel benzopyrans having pharmacological activity, to a process for preparing them, to pharmaceutical compositions containing them, and to their use in the treatment of hypertension.

European Patent Publication No. 158,923 discloses classes of chromans that are described as having blood pressure lowering activity.

The present invention discloses compounds represented by formula (I)

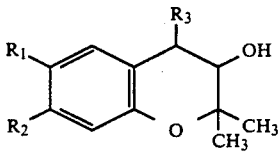

wherein $R_1$ and $R_2$ are independently selected from the group consisting of H, halogen, F, $C_1$ to $C_7$ alkyl, $C_3$ to $C_7$ cycloalkyl, cyano, nitro, trifluoromethyl, trifluoromethoxy, trifluoroethoxy, $C_1$ to $C_7$ alkoxy, $C_1$ to $C_7$ alkylcarbonyl, $C_3$ to $C_7$ cycloalkylcarbonyl, $C_1$ to $C_7$ thio alkyl, $C_1$ to $C_7$ sulfoxy alkyl, $C_1$ to $C_7$ sulfonyl alkyl, amino, $C_1$ to $C_7$ mono- or disubstituted amino, $C_1$ to $C_7$ mono- or disubstituted amino; $R_3$ is selected from the group consisting of

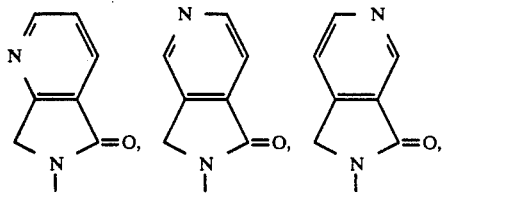

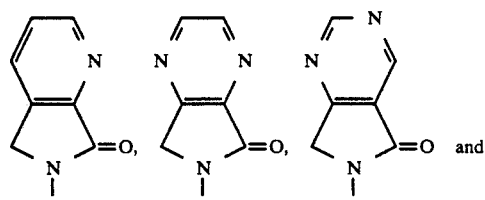

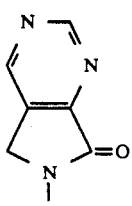

Also disclosed are N-oxides and pharmaceutically acceptable salts thereof.

A preferred aspect of the present invention are compounds of formula (II)

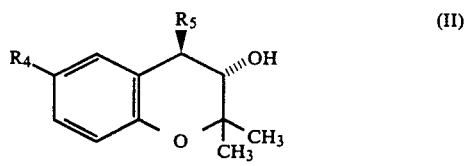

wherein $R_4$ is selected from the group consisting of H, F, trifluoromethoxy, trifluoromethyly, $C_1$ to $C_7$ alkoxy, cyano, nitro, $C_1$ to $C_7$ alkylcarbonyl or $C_3$ to $C_7$ cycloalkylcarbonyl; $R_5$ is selected from the group consisting of

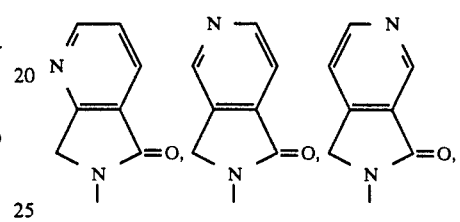

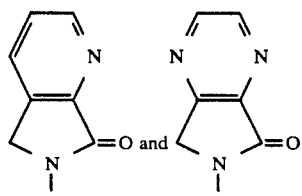

the N-oxides and pharmaceutically acceptable salts thereof.

A further preferred aspect of the present invention are the compounds:

6-[(trans)-3,4-dihydro-3-hydroxy-2,2-dimethyl-6-(trifluoromethoxy)-2H-1-benzopyran-4-yl]-6,7-dihydro-5H-pyrrolo[3,4-b]pyridin-5-one;

(trans)-6-[3,4-dihydro-3-hydroxy-2,2-dimethyl-6-(trifluoromethoxy)-2H-1-benzopyran-4-yl]-5,6-dihydro-7H-pyrrolo[3,4-b]pyridin-7-one;

(trans)-2-[3,4-dihydro-3-hydroxy-2,2-dimethyl-6-(trifluoromethoxy)-2H-1-benzopyran-4-yl]-1,2-dihydro-3H-pyrrolo[3,4-c]pyridin-3-one;

(trans)-2-[3,4-dihydro-3hydroxy-2,2-dimethyl-6-(trifluoromethoxy)-2H-1-benzopyran-4-yl]-2,3-dihydro-1H-pyrrolo[3,4-c]pyridin-1-one;

(trans)-6-[3,4-dihydro-3-hydroxy-2,2-dimethyl-6-(trifluoromethoxy)-2H-1-benzopyran-4-yl]-6,7-dihydro-5H-pyrrolo[3,4-b]pyrazin-5-one;

and the pharmaceutically acceptable salts thereof.

The compounds of formula (I), are asymmetric and, therefore, can exist in the form of optical isomers. The present invention extends to all such isomers individually and as mixtures, such as racemic modifications.

Preferably, a compound of formula (I) is in substantially pure form.

Examples of compounds of formula (I) include the compounds prepared in the Examples hereinafter.

The present invention also provides a process for the preparation of a compound of formula (I), which is exemplified by the reaction of a compound of formula (V)

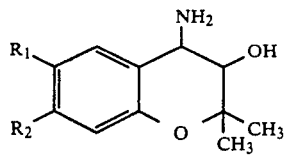

wherein $R_1$ and $R_2$ are as defined hereinbefore with a compound of formula (VI) to (XII)

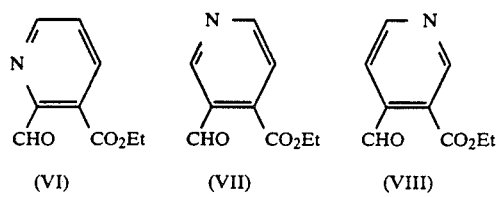

It is particularly preferred that the reaction between the compounds of formula (V) and (VI) to (XII) is carried out under alkylation conditions so as to facilitate the formation of the desired bonds, for example, by heating in the presence of $ZnCl_2 \cdot NaCNBH_3$ in ethanol.

The compounds of formula (VI) to (XII) can be prepared by the same process for the preparation of the compound of formula (VI) set forth below.

The production of preferred compounds of the present invention is illustrated by Synthetic Process B.

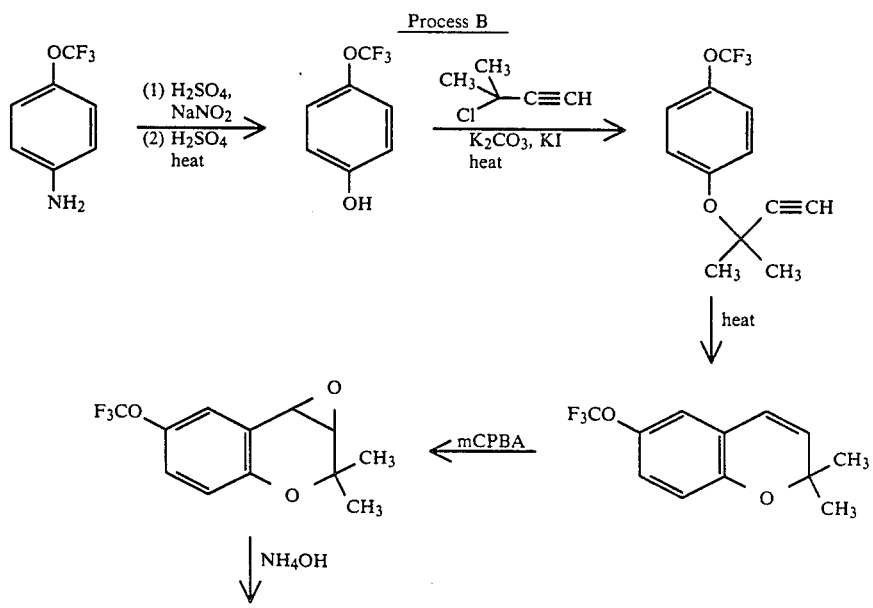

Process B

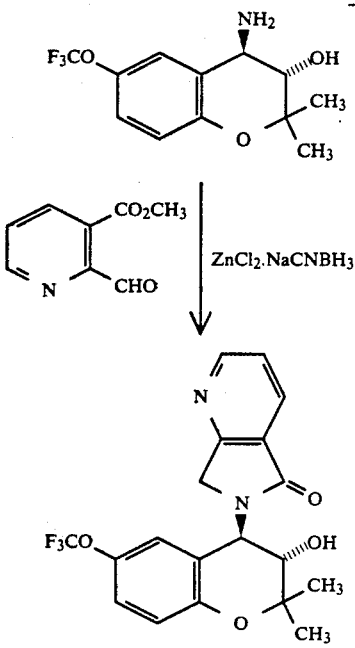

The compounds of formula (I) can be converted to the corresponding N-oxides by treatment with hydrogen peroxide by conventional means.

The compounds of this invention are capable of forming acid addition salts with therapeutically acceptable acids. The acid addition salts are prepared by reacting the base form of the appropriate compound of formula (I) with one or more equivalents, preferably with an excess, of the appropriate acid in an organic solvent, for example diethyl ether or an ethanol diethyl ether mixture.

These salts, when administered to a mammal, posses the same or improved pharmacologic activities as the corresponding bases. For many purposes it is preferable to administer the salts rather than the basic compounds. Suitable acids to form these salts include the common mineral acids, e.g. hydrohalic, sulfuric or phosphoric acid; the organic acids, e.g. ascorbic, citric, lactic, aspartic or tartaric acid; and acids which are sparingly soluble in body fluids and which impart slow-release properties to their respective salts, e.g. pamoic or tannic acid or carboxymethyl cellulose. The preferred salt is the hydrochloride salt. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The compounds of formula (V) are novel compounds and can be prepared in accordance with the processes described herein.

The compounds of formula (VI) to (XII) are known compounds or can be prepared by conventional procedures from known compounds.

As mentioned previously, the compounds of formula (I) have been found to have blood-pressure lowering activity. They are therefore useful in the treatment of hypertension.

Since the compounds of the present invention are believed to be $K^+$ channel openers, they could also have utility in the treatment of heart failure; in the treatment of peripheral vascular disease; for hair growth stimulation; and as bronchodialators in the treatment of asthma.

The present invention accordingly provides a pharmaceutical composition which comprises a compound of this invention and a pharmaceutically acceptable carrier. In particular, the present invention provides an anti-hypertensive pharmaceutical composition which comprises an antihypertensive effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

The present invention further provides a compound of the invention for use as an active therapeutic substance. Compounds of formula (I) are of particular use in the treatment of hypertension.

The present invention further provides a method of treating hypertension in mammals including man, which comprises administering to the afflicted mammal an antihypertensive effective amount of a compound or a pharmaceutical composition of the invention.

The resolution of compounds of formula (I) into optical isomers may be accomplished by reacting the reacemate with an optically pure chiral auxiliary, preferable 1-(1-naphthyl)ethyl isocyanate or α-methylbenzyl isocyanate, to form a mixture of two diastereomers. These diastereomers are then separated by physical means, such as chromatography or crystallization. Each is reacted to remove the chiral auxiliary to afford the enantiomers of compounds of formula (I).

The resolution of compounds of formula (I) into optical isomers may also be accomplished by the resolution process described in Soll et al, AHP-9458, serial number not yet known.

The following Examples further illustrate this invention.

EXAMPLE 1

Preparation of p-Trifluoromethoxy Phenol p-Trifluoromethoxy aniline (49.60 g) was added rapidly dropwise to vigorously stirred 9N aqueous $H_2SO_4$(500 mL) at 40° C. The mixture was heated to dissolve the solid, then cooled to 0° C. To the fine white suspension, a solution of sodium nitrite (19.46 g in 50 mL of $H_2O$) was added portionwise until an immediate positive KI/starch test result was obtained. This cold solution of diazonium salt was added rapidly dropwise to 9N aqueous $H_2SO_4$(500 mL) at 110° C. Stirring and heating was continued for 2.5 hours. The mixture was cooled to 10° C. and extracted with diethyl ether (3×500 mL). The combined organic layers were dried ($MgSO_4$), filtered and evaporated in vacuo, then flash chromatographed on $SiO_2$ using diethyl ether as eluant to give 35.0 g of the desired phenol as a light brown oil. The oil was distilled (b.p.=75°–80° C. at 20 torr.) to afford a yellow liquid.

NMR (CDCl$_3$): δ 5.06 (1H, s), 6.83 (2H, d, J=9.2), 7.11 (2H, d, J=9.2 Hz).

EXAMPLE 2

Preparation of 1-[(1,1-Dimethyl-2-propynyl)oxy]-4-(trifluoromethoxy)benzene

To a solution of p-trifluoromethoxy phenol (30.69 g), and 2-methyl-2-chloro-3-butyne (53.00 g) in dry acetonitrile (350 mL) was added potassium iodide (14.30 g) followed by potassium carbonate (95.25 g). This reaction mixture was heated at 70°–80° C. for four days then cooled to room temperature and filtered through celite. The precipitate was washed with dichloromethane and the washings were added to the acetonitrile. The organics were evaporated in vacuo and the oil was taken up in 250 mL of dichloromethane. The organics were washed with water (2×100 mL) and dilute aqueous sodium thiosulfate (2×100 mL), dried ($MgSO_4$), filtered and evaporated in vacuo to leave a dark brown-orange oil. Flash chromatography on $SiO_2$ using hexane/$Et_2O$ (5/1) afforded 34.73 g of the pure product.

NMR (CDCl$_3$): δ 1.64 (6H, s), 2.60 (1H, s), 7.05–7.30 (4H, m).

EXAMPLE 3

Preparation of 2,2-Dimethyl-6-(trifluoromethoxy)-2H-1-benzopyran

A solution of 1-[(1,1-dimethyl-2-propynyl)oxy]-4-trifluoromethoxybenzene (16.25 g) in 60 mL of quinoline was heated to 175° C. for 2 hours. The solution was cooled to room temperature then ether (250 mL) was added. This mixture was stirred for 15 minutes then decanted from any precipitated tars. The ether solution was washed with 1N aqueous hydrochloric acid (3×200 mL) then water (1×200 mL) and dried ($K_2CO_3$). The filtered ether solution was evaporated and flash chromatographed on $SiO_2$ using hexane/ethyl acetate (5/1) as eluant to afford 13.92 g (85%) of the desired bicyclic compound.

Alternate Preparation of 2,2-Dimethyl-6-(trifluoromethoxy)-2H-1-benzopyran

A solution of the 1-[(1,1-dimethyl-2-propynyl)oxy]-4-trifluoromethoxybenzene (29.05 g) in 100 mL of chlorobenzene (b.p.=132° C.) was heated to reflux for 24 hours. The reaction mixture was cooled and the solvent removed in vacuo. The oily residue was flash chromatographed on $SiO_2$ using hexane/ethyl acetate (5/1) as eluant to afford 19.72 g of the desired bicyclic compound.

NMR (CDCl$_3$): δ 1.42 (6H, s), 5.67 (1H, d, J=10 Hz), 6.28 (1H, d, J=10 Hz), 6.78 (1H, d, J=5.5 Hz), 6.83 (1H, d, J=2H), 6.94 (1H, dd, J=5.5 Hz, 2 Hz).

EXAMPLE 4

Preparation of 1a,7b-Dihydro-2,2-6-(trifluoromethoxy)-2H-oxireno[c][1]benzopyran To a solution of 2,2-dimethyl-6-trifluoromethoxy-2H-1-benzopyran (14.37 g) in dichloromethane (40 mL) at 0° C. was added a solution of m-chloroperoxybenzoic acid (mCPBA, 14.22 g) in dichloromethane (160 mL) dropwise. After the solution was complete the ice bath was removed and the temperature allowed to warm slowly to 15° C. while stirring for 18 hours. The reaction mixture was filtered, and the precipitate was washed with dichloromethane (50 mL). The combined filtrate was washed with 25% aqueous sodium thiosulfate (2×100 mL), and 50% aqueous sodium bicarbonate (2×100 mL), dried ($MgSO_4$), filtered and evaporated in vacuo. The orange oil was flash chromatographed on $SiO_2$ using hexane/ether (4/1) as eluant to afford 13.36 of the epoxide as a light yellow oil, which solidified upon standing.

NMR (CDCl$_3$): δ 1.25 (3H, s), 1.58 (3H, s), 3.49 (1H, d, J=4Hz), 3.86 (1H, d, J=4 Hz), 6.78 (1H, d, J=8.5 Hz), 7.11 (1H, dd, J=8.5 Hz and 2 Hz), 7.22 (1H, d, J=2 Hz).

EXAMPLE 5

Preparation of trans-2,3-Dihydro-2,2-dimethyl-3-hydroxy-6-(trifluoromethoxy)-2H-1-benzopyran-4-amine To a solution of 1a,7b-dihydro-2,2-dimethyl-6-(trifluoromethoxy)-2H-oxireno[c][1]benzopyran (6.18 g) in absolute ethanol (30 mL) at 0° C. was added ammonium hydroxide (45 mL). The reaction mixture was capped with a rubber septum and stirred for four days. The reaction mixture was evaporated in vacuo to remove ethanol and water and the oil was taken up in dichloromethane, dried (Na$_2$SO$_4$) filtered and concentrated in vacuo. The residue was flash chromatographed on SiO$_2$ using dichloromethane/methanol (5/1) as eluant to afford the amino-alcohol, m.p. 176°–182° C. (dec.) recrystallized from ethyl ether/hexane.

Two of the above reactions were run simultaneously to obtain of 8.95 g of product.

NMR (DMSO—d$_6$): δ 1.07 (3H, s), 1.35 (3H, s), 3.20 (1H, d, J=9.2 Hz), 3.52 (1H, d, J=9.2 Hz), 6.76 (1H, d, J=9 Hz), 7.08 (1H, dd, J=9 Hz, 1.5 Hz), 7.51 (1H, d, J=1.5 Hz).

EXAMPLE 6

Preparation of 2.3-Pyridinedicarboxylic Acid Diethyl Ester

To a slurry of 2,3-pyridinecarboxylic acid (11.84 g, 70.847 mmol) in ethanol (250 mL) was added p-toluenesulfonic acid (1.26 g, 7.08 mmol). After refluxing for 4 days, ethanolic HCl was added (3 g HCl g dissolved in 25 mL EtOH). After another 2 days at reflux, the solution was cooled, carefully quenched with saturated NaHCO$_3$ and concentrated to ~⅓ volume. Redissolved in EtOAc (500 mL) and washed with saturated NaHCO$_3$ (2×300 mL), saturated brine (1×300 mL), dried over MgSO$_4$, filtered, concentrated, and vacuum distilled (152° C. at 2.8 mm) to provide 9.28 g of a light yellow oil (58.7%).

$^1$H NMR (CDCl$_3$, 200 MHz): δ 8.76 (d, 1H, Arom), 5.19 (d, 1H, Arom), 7.48 (dd, 1H, Arom), 4.43 (m, 4H, 2 OC$\underline{H}_2$), 1.41 (m, 6H, 2 CH$_3$).

EXAMPLE 7

Preparation of Ethyl 2-Formylnicotinate

In flame-dried glassware under N$_2$ atmosphere, to a solution of 2,3-pyridinedicarboxylic acid diethyl ester (0.254 g, 1.14 mmol) in anhydrous toluene (5 mL) at −78° C. was added diisobutylaluminum hydride (DiBal) (1.48 mL, 1.48 mmol, 1M in toluene). After 30 minutes, additional DiBal (0.4 mL, 0.4 mmol, 1M in toluene) was added. After 15 minutes, the reaction mixture was quenched with methanol (2 mL)/saturated Na/K tartrate (40 mL) and extracted into EtOAc (3×50 mL). The combined organic extracts were washed with saturated NaHCO$_3$ (2×50 mL), saturated brine (1×75 mL), dried over MgSO$_4$, filtered, concentrated, and flash chromatographed (5 to 10% EtOAc/CH$_2$Cl$_2$ gradient) to provide 0.075 g of the title compound as a colorless oil (36.8%). $^1$H NMR (CDCl$_3$, 300 MHz): δ 10.34 (s, 1H, RCHO), 8.84 (d, 1H, Arom), 8.10 (d, 1H, Arom), 7.56 (dd, 1H, Arom), 4.45 (q, 2H, OC$\underline{H}_2$), 1.40 (t, 3H, CH$_2$C$\underline{H}_3$)

MS: (+FAB) 180 (M+$\overline{H}$)+.

EXAMPLE 8

Preparation of 6-[(trans)-3,4-Dihydro-3-hydroxy-2,2-dimethyl-6-(trifluoromethyoxy)-2H-1-benzopyran-4-yl]-6,7-dihydro-5H-pyrrolo[3,4-b]pyridin-5-one To a solution of trans-2,3-dihydro-2,2-dimethyl-3-hydroxy-6-(trifluoromethoxy)-2H-1-benzopyran-4-amine (0.832 g, 3.00 mmol) in dry ethanol (30 mL) was added ethyl 2-formylnicotinate (0.644 g, 3.30 mmol) and this was stirred for 30 minutes. To this solution, at room temperature, was added zinc chloride-sodium cyanoborohydride solution (9 mL, 0.5M in methanol) via syringe. After two hours, the solution was warmed to 50° C. for 10 hours. The mixture was cooled, saturated aqueous sodium bicarbonate (18 mL) was added and the mixture stirred for 30 minutes. The ethanol was removed in vacuo and the aqueous layer was extracted with dichloromethane (2×40 mL). The organics were combined, washed with water (2×50mL), dried (K$_2$CO$_3$) and evaporated to leave a clear oil.

This oil was taken up in hot toluene/hexane (30 mL/10 mL) and heated to reflux for five hours. The mixture was cooled slowly to −10° C. (ice/methanol bath) and stirred at that temperature for 1 hour. The resulting solid was collected by vacuum filtration, and the solid was washed with cold heptane to afford, after drying in the vacuum oven, 640 mg of a white solid (54.1%).

$^1$H NMR (CDCl$_3$, 400 MHz): δ 8.68 (1H, dd, Arom), 8.04 (1H, dd, Arom), 7.35 (1H, dd, Arom), 7.07 (1H, dd, Aron), 6.80 (1H, d, Arom), 6.71 (1H, d, Arom), 5.62 (1H, d, J=10.1 Hz), 4.25 (2H, AB quartet, J=17.63 and 83.17 Hz), 3.96 (1H, dd, J=10.13 and 5.98 Hz), 3.67 (1H, d, J=5.96 Hz), 1.59 (3H, s) and 1.38 (3H, s).

IR(cm$^{-1}$): 3250 (br), 1682 (s), 1670 (s), 1600 (m), 1580 (m), 1480 (s), 1235 (s), 1200 (s) and 1160 (s).

MS: [CI(+)] 395 (MH+).

Anal. Calcd.: C, 57.87; H, 4.34; N, 7.10. Found: C, 57.54; H, 4.24; N, 7.07.

EXAMPLE 9

Preparation of N-Phenyl-2-pyridinecarboxamide

To a solution of carbonyldiimidazole (8.10 g) in dry dimethylformamide (100 mL) under N$_2$ atmosphere, was added the picolinic acid (15.0 g) portionwise, then stirred for 30 minutes. Aniline (10.93 mL) was added rapidly dropwise, then stirred for 18 hours at room temperature. The reaction mixture was poured into water (400 mL), basified with 2.5N NaOH (25 mL) and stirred for 30 minutes while solid precipitated. The solid was collected by vacuum filtration, washed with water, and dried in vacuo. This tan solid was recrystallized from ether/hexane (1/1) to afford 7.69 g (32.3%) of an off-white solid, m.p. 75°–77° C.

$^1$H NMR (CDCl$_3$): δ 10.06 (1H, br s) and 7.05–8.65 (9H, series of m).

EXAMPLE 10

Preparation of 5,6-Dihydro-5-hydroxy-6-phenyl-7H-pyrrolo-[3,4-b]pyridin-7-one

To a solution of N-phenyl-2-pyridinecarboxamide (1.00 g) in dry tetrahydrofuran (20 mL) under N$_2$ atmosphere at −78° C., was added n-butyllithium in hexane (4.0 mL, 2.5M). This mixture was allowed to stir for one hour. Methyl formate (0.62 mL) in dry tetrahydrofuran (5 mL) was added rapidly dropwise. After addition, the cold bath was removed and the mixture warmed to room temperature over two hours. The reaction was quenched with water and the tetrahydrofuran was evaporated in vacuo. The residue was extracted with ethyl acetate and dried (K$_2$CO$_3$). Purification was effected by flash chromatography on silica gel using ethyl acetate/hexane (6/4) as eluant (R$_f$=0.1). The yield was 310 mg (27.4%).

$^1$H NMR (DMSO—d$_6$): δ 8.83 (1H, d, J=5.0 Hz), 8.15 (1H, d, J=7.0 Hz), 7.20–7.83 (6H, series of m), 6.96 (1H, d, J=9.5 Hz) and 6.58 (1H, d, J=9.5 Hz).

EXAMPLE 11

Preparation of 3-(Dimethoxymethyl)-2-pyridinecarboxylic Acid Methyl Ester

To a solution of 5,6-dihydro-5-hydroxy-6-phenyl-7H-pyrrolo[3,4-b]pyridin-7-one (1.99 g) in 100 mL of methanol was added concentrated sulfuric acid (6 mL). The reaction mixture was warmed to 75° C. for 3 hours. TLC indicated that all starting material had been converted. The reaction mixture was neutralized with aqueous sodium bicarbonate and evaporated in vacuo to remove the methanol. The aqueous residue was extracted with ether (3×). The organic extracts were combined, dried ($K_2CO_3$) and evaporated. The product was isolated by flash chromatography on silica gel using ethyl ether/hexane (3/2) as eluant to yield 1.02 g (59.4%).

$^1$H NMR (CDCl$_3$): δ 8.65 (1H, dd, J=4.4 Hz and 1.3 Hz), 8.12 (1H, dd, J=8.0 Hz and 1.3 Hz), 7.48 (1H, dd, J=8.0 Hz and 4.4 Hz), 6.05 (1H, s), 4.02 (3H, s) and 3.40 (6H, s).

EXAMPLE 12

Preparation of 3-Formyl-2-pyridinecarboxylic Acid Methyl Ester

To a solution of 3-(dimethoxymethyl)-2-pyridinecarboxylic acid methyl ester (1.02 g) in dioxane (20 mL) was added water (20 mL), followed by p-toluenesulfonic acid (0.3 g). This solution was heated at 55°–60° C. for 24 hours. The reaction mixture was cooled, diluted with water (50 mL), treated with aqueous saturated sodium bicarbonate until the pH was 7.5–8.0, and extracted with methylene chloride (3×). The combined organic extracts were washed with dilute brine (3×), dried ($K_2CO_3$) and evaporated to afford a light yellow solid which yielded 540 mg (62.5%) of an almost pure product.

$^1$H NMR(CDCl$_3$): δ 10.68 (1H, s), 8.90 (1H, dd, J=4.7 Hz and 1.4 Hz), 8.31 (1H, dd, J=7.8 Hz and 1.4 Hz), 7.65 (1H, dd, J=7.8 Hz and 4.7 Hz), and 4.10 (3H, s).

EXAMPLE 13

Preparation of (trans)-6-[3,4-Dihydro-3-hydroxy-2,2-dimethyl-6-(trifluoromethoxy)-2H-1-benzopyran-4-yl]-5,6-dihydro-7H-pyrrolo[3,4-b]pyridin-7-one A solution of trans-2,3-dihydro-2,2-dimethyl-3-hydroxy-6-(trifluoromethyoxy)-2H-1-benzopyran-4-amine, prepared by the process of Example 5 (0.83 g) and 3-formyl-2-pyridinecarboxylic acid methyl ester (0.54 g) in methanol (65 mL) was stirred for 30 minutes. To this solution was added sodium cyanoborohydride-zinc chloride solution (12 mL of 0.5M solution in methanol) and stirring was continued for 45 minutes at room temperature, then heated to 50° C. for 16 hours. The cooled mixture was quenched with saturated aqueous sodium bicarbonate (12 mL) and stirred for 10 minutes. The methanol was evaporated in vacuo, water (50 mL) was added, and the mixture was extracted with ethyl acetate (3×125 mL). The combined extracts were washed with water (2×100 mL), dried ($K_2CO_3$) and evaporated. The foamy residue was dissolved in hot toluene (25 mL) and heated at reflux for 2 hours. The solution was cooled and evaporated to dryness. The foamy residue was flash chromatographed on silica gel using ethyl acetate as eluant. The pure material so obtained was crystallized from warm methylene chloride/hexane (1/1) to afford 607 mg of desired compound, yield 51.3%, m.p. 248°–250° C.

$^1$H NMR (CDCl$_3$): δ 8.72 (1H, d, J=4.2 Hz), 7.79 (1H, d, J=7.0 Hz), 7.41 (1H, dd, J=4.2 Hz and 7.0 Hz), 7.08 (1H, br d, J=9.0 Hz), 6.88 (1H, d, J=9.0 Hz), 6.75 (1H, br s), 5.71 (1H, d, J=10.1 Hz), 4.43 (1H, d, J=17.2 Hz, AB system), 4.15 (1H, d, J=17.2 Hz, AB system), 3.95 (1H, d, J=10.1 Hz), 3.60 (1H, br), 1.58 (3H, s) and 1.38 (3H, s).

MS (EI): M+ (394).

Anal. Calcd.: C, 57.87; H, 4.35; N, 7.1. Found: C, 57.82; H, 4.23; N, 7.0.

PHARMACOLOGICAL DATA

Spontaneously hypertensive rats (SHR) of the Okamoto-Aoki strain ranging in weight from 300–370 g were used for these experiments. Each rat was anesthetized with halothane and a femoral artery and vein cannulated with polyethylene tubing of the appropriate size (i.d., 0.023", o.d., 0.038"). The animals were placed into Bollman cages for restraint purposes during the experiment. The femoral arterial cannula was connected to a Gould Statham pressure transducer which in turn was attached to a polygraph for recording of arterial blood pressure and pulse rate. The pulse rate was considered to be equivalent to the heart rate. The animals were allowed one hour to recover from anesthesia before the test compound, dispersed in a 0.5%, solution of methylcellulose, was administered by gastric gavage in a volume of 5 mL/kg. Mean arterial pressure was recorded prior to and continuously for up to 24 hours after dosing while heart rate was recorded prior to and at 5, 10, 15, 30, 45, 60, 120, 180, 240 minutes, and again at 24 hours after drug administration. For each dose, the maximum fall in blood pressure was given in mmHg and also expressed as a percentage decrease compared to pretreatment control values. Linear regression on the maximum decrease in mean arterial blood pressure at each dose was used to calculate the ED$_{30}$ (the dose which would lower mean arterial pressure by 30%). A decrease in mean arterial blood pressure of 30% reduces the blood pressure from the hypertensive to the normotensive range. The results of oral administration of various doses of the compounds of this invention are given in the accompanying table.

Blood Pressure Lowering by Compounds of Formula (II)

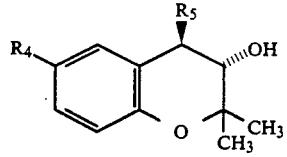

(II)

| R4 | R5 | mg/kg p.o. | n | Pretreat. MABP mm Hg | Blood Pressure ΔBP mm Hg | % | Pretreat. HR beats/min | Heart Rate ΔHR beats | % |
|---|---|---|---|---|---|---|---|---|---|
| —OCF3 | (pyrrolo-pyridinone, N down) | 10 | 4 | 167 | −100 (30 min)<br>−95 (4 hr)<br>−64 (24 hr) | −60<br>−57<br>−38 | 369 | +60 (4 hr) | +16 |
| | | 2.5 | 7 | 184 ± 3 | −74 (4 hr)<br>−51 (24 hr) | −40<br>−28 | 390 ± 7 | +66 (4 hr) | +17 |
| | | 1 | 7 | 187 ± 5 | −59 (4 hr)<br>−22 (24 hr) | −32<br>−12 | 377 ± 17 | +62 (4 hr) | +16 |
| | | 0.5 | 7 | 186 ± 4 | −52 (5 hr)<br>−19 (24 hr) | −28<br>−10 | 388 ± 6 | +69 (4 hr) | +18 |
| | | 0.25 | 7 | 179 ± 3 | −26 (4 hr)<br>−28 (7 hr)<br>−9 (24 hr) | −15<br>−16<br>−5 | 377 ± 17 | +28 (4 hr) | +7 |
| | | 0.1 | 4 | 173 ± 4 | −11 (3 hr) | −6 | 374 ± 19 | +6 (3 hr) | +2 |
| —OCF3 | (pyrrolo-pyridinone, N up) | 0.1 | 4 | 178 ± 5 | −15 (4 hr) | −8 | 388 ± 10 | ±35 (4 hr) | +9 |
| | | 0.5 | 3 | 187 ± 8 | −54 (45 min)<br>−57 (4 hr)<br>(24 hr) | −29<br>−30<br>−15 | 382 ± 12 | +74 (45 min) | +19 |
| | | 2.5 | 2 | 214 ± 12 | −133 (30 min)<br>−95 (24 hr) | −62<br>−44 | 425 ± 11 | +24 (30 min) | +6 |
| | | 10 | 4 | 179 ± 8 | −108 (30 min)<br>−105 (4 hr)<br>(24 hr) | −60<br>−59<br>−58 | 367 ± 12 | +93 (30 min) | +25 |
| Control 0.5% Methylcellulose | | 0 | 8 | 181 ± 3 | −7 (30 min)<br>−5 (4 hr)<br>−6 (24 hr) | −4<br>−3<br>−4 | 394 ± 14 | +17 (30 min)<br>+1 (4 hr) | +5<br>0 |

The calculated ED30 for 6-[(trans)-3,4-dihydro-3-hydroxy-2,2-dimethyl-6-(trifluoromethoxy)-2H-1-benzopyran-4-yl]-6,7-dihydro-5H-pyrrolo[3,4-b]pyridin-5-one (the dose calculated to lower blood pressure by 30%) is 0.8 mg/kg p.o.

Compounds of formula (I) may be administered alone or with a diuretic, such as hydrochlorothiazide, or a β-blocker, such as propranolol or cetamolol in a suitable unit dose form.

We claim:

1. A compound of formula (I)

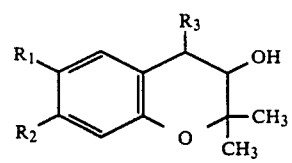

(I)

wherein $R_1$ and $R_2$ are independently selected from the group consisting of H, halogen, F, $C_1$ to $C_7$ alkyl, $C_3$ to $C_7$ cycloalkyl, cyano, nitro, trifluoromethyl, trifluoromethoxy, trifluoroethoxy, $C_1$ to $C_7$ alkoxy, $C_1$ to $C_7$ alkylcarbonyl, $C_3$ to $C_7$ cycloalkylcarbonyl, $C_1$ to $C_7$ thio alkyl, $C_1$ to $C_7$ sulfoxy alkyl, $C_1$ to $C_7$ sulfonyl alkyl, amino, $C_1$ to $C_7$ mono-or disubstituted amino, $C_1$ to $C_7$ mono- or disubstituted amido; $R_3$ is selected from the group consisting of

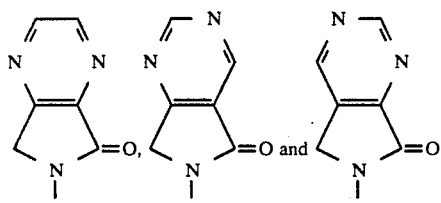

and the N-oxides and pharmaceutically acceptable salts thereof.

2. The compound according to claim 1 of formula (II)

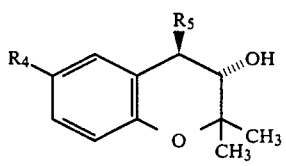

wherein $R_4$ is selected from the group consisting of H, F, trifluoromethoxy, trifluoromethyl, $C_1$ to $C_7$ alkoxy, cyano, nitro, $C_1$ to $C_7$ alkylcarbonly or $C_3$ to $C_7$ cycloalkylcarbonyl; $R_5$ is

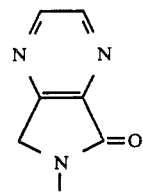

and the N-oxides and pharmaceutically acceptable salts thereof.

3. The compound according to claim 2 which is (trans)-6-[3,4-dihydro-3-hydroxy-2,2-dimethyl-6-(trifluoromethoxy)-2H-1-benzopyran-4-yl]-6,7-dihydro-5H-pyrrolo[3,4-b]pyrazin-5-one and the pharmaceutically acceptable salts thereof.

4. A pharmaceutical composition comprising an effective amount of a compound according to claim 1 or an N-oxide or a pharmaceutically acceptable salt thereof and a pharmaceutically acceptable carrier for use in the treatment of hypertension.

5. A method of treatment of hypertension in mammals which comprises administering to the mammal in need thereof an effective antihypertensive amount of a compound of formula (I) an N-oxide or a pharmaceutically acceptable salt thereof.

* * * * *